US005563071A

United States Patent [19]

Augurt

[11] Patent Number: 5,563,071
[45] Date of Patent: Oct. 8, 1996

[54] METHOD, REAGENT AND KIT FOR THE DETECTION OF FECAL OCCULT BLOOD

[75] Inventor: Thomas A. Augurt, New Canaan, Conn.

[73] Assignee: Propper Manufacturing Co., Inc., Long Island City, N.Y.

[21] Appl. No.: 439,603

[22] Filed: May 12, 1995

Related U.S. Application Data

[62] Division of Ser. No. 121,072, Sep. 14, 1993, Pat. No. 5,447,868.

[51] Int. Cl.$^6$ ................................................. G01N 33/72
[52] U.S. Cl. ............................ 436/66; 436/904; 422/61; 435/28; 435/810
[58] Field of Search ................................ 422/56, 57, 58, 422/61; 436/66, 8, 19, 164, 169, 904; 435/28, 805, 810

[56] References Cited

U.S. PATENT DOCUMENTS

| | | | |
|---|---|---|---|
| 3,290,117 | 12/1966 | Adams et al. | 422/56 |
| 3,975,161 | 8/1976 | Svoboda et al. | 422/56 |
| 3,986,833 | 10/1976 | Mast et al. | 436/66 |
| 3,996,006 | 12/1976 | Pagano | 422/50 |
| 4,017,261 | 4/1977 | Svoboda et al. | 422/56 |
| 4,063,894 | 12/1977 | Ogawa et al. | 436/66 |
| 4,071,315 | 1/1978 | Chateau | 436/518 |
| 4,071,317 | 1/1978 | Lam | 422/56 |
| 4,071,318 | 1/1978 | Lam | 422/56 |
| 4,071,321 | 1/1978 | Lam | 436/66 |
| 4,219,336 | 8/1980 | Guthlien et al. | 436/66 |
| 4,220,713 | 9/1980 | Rittersdorf | 435/14 |
| 4,247,631 | 1/1981 | Nix et al. | 435/10 |
| 4,279,993 | 7/1981 | Magers et al. | 435/14 |
| 4,290,773 | 9/1981 | Magers et al. | 436/169 |
| 4,302,537 | 11/1981 | Gübdermann et al. | 435/7.4 |
| 4,333,734 | 6/1982 | Fleisher | 436/66 |
| 4,460,684 | 7/1984 | Bauer | 435/14 |
| 4,486,536 | 12/1984 | Baker et al. | 436/66 |
| 4,493,892 | 1/1985 | Fleischer | 435/28 |
| 4,543,338 | 9/1985 | Chen | 436/170 |
| 4,562,043 | 12/1985 | Mennen et al. | 422/56 |
| 4,587,220 | 5/1986 | Mayambala-Mwanika et al. | 436/66 |
| 4,615,982 | 10/1986 | Lawrence | 436/66 |
| 4,645,743 | 2/1987 | Baker et al. | 436/66 |
| 4,719,181 | 1/1988 | Schobel et al. | 436/66 |
| 4,742,002 | 5/1988 | Guadagno | 435/28 |
| 4,778,753 | 10/1988 | Yamanishi et al. | 435/10 |
| 4,789,629 | 12/1988 | Baker et al. | 422/61 X |
| 4,818,702 | 4/1989 | Lawrence | 436/66 |
| 4,820,646 | 4/1989 | Lawrence | 436/66 |
| 4,828,983 | 5/1989 | McClune | 435/7.92 |
| 4,891,314 | 1/1990 | Pauly et al. | 435/28 |
| 4,895,798 | 1/1990 | Charlton et al. | 435/14 |
| 4,920,045 | 4/1990 | Okuda et al. | 435/7.1 |
| 4,937,197 | 6/1990 | Lawrence | 436/66 |
| 4,939,097 | 7/1990 | Lawrence | 436/66 |
| 4,942,132 | 7/1990 | Lawrence | 436/66 |
| 4,971,914 | 11/1990 | Lawrence | 436/66 |
| 5,013,669 | 5/1991 | Peters, Jr. et al. | 436/518 |
| 5,053,342 | 10/1991 | Lawrence | 436/66 |
| 5,064,766 | 11/1991 | Wardlaw et al. | 436/66 |
| 5,068,197 | 11/1991 | Lawrence | 436/66 |
| 5,081,040 | 1/1992 | Patel et al. | 436/66 |
| 5,084,382 | 1/1992 | Frey et al. | 435/28 |
| 5,084,395 | 1/1992 | Bouse et al. | 436/166 |
| 5,089,420 | 2/1992 | Albarella et al. | 436/66 |
| 5,094,956 | 3/1992 | Grow et al. | 436/66 |
| 5,122,451 | 1/1992 | Tanaka et al. | 435/74 |
| 5,178,831 | 1/1993 | Sakota et al. | 422/56 |
| 5,196,167 | 3/1993 | Guadagno et al. | 422/56 |
| 5,310,680 | 5/1994 | Baker et al. | 436/66 |
| 5,391,498 | 2/1995 | Baker et al. | 436/66 |
| 5,447,868 | 9/1995 | Augurt | 436/66 |

FOREIGN PATENT DOCUMENTS

| | | |
|---|---|---|
| 844973 | 2/1977 | Belgium . |
| 0253548 | 1/1988 | European Pat. Off. . |
| 0308227 | 3/1989 | European Pat. Off. . |
| 1147366 | 6/1989 | Japan . |
| 1560077 | 1/1980 | United Kingdom . |
| 8603585 | 6/1986 | WIPO . |
| 8905972 | 6/1989 | WIPO . |

OTHER PUBLICATIONS

Abstract–JP 1–147366, Jun. 9, 1989. (Derwent–World Patent Index).

*Primary Examiner*—Jill Warden
*Assistant Examiner*—Maureen M. Wallenhorst
*Attorney, Agent, or Firm*—Oppedahl & Larson

[57] ABSTRACT

A fecal specimen may be tested for the presence of occult blood by combining the fecal specimen with (a) an oxidizable substrate that produces a colored product in the presence of peroxide and hemoglobin;

(b) hydrogen peroxide or a peroxide source; and (c) an enhancer selected to enhance the sensitivity of the test. Suitable enhancers are monocyclic nitrogen-containing aromatic heterocyclic compounds; tertiary or quaternary ammonium compounds having a phenyl, hydroxy alkyl or esterified hydroxy alkyl attached to the nitrogen; or quinoline or a substituted derivative thereof. If hemoglobin is present in the fecal sample, the oxidizable substrate is converted to the visibly detectable, colored product.

17 Claims, No Drawings

METHOD, REAGENT AND KIT FOR THE DETECTION OF FECAL OCCULT BLOOD

SPECIFICATION

This application is a divisional of U.S. patent application Ser. No. 08/121,072 filed Sep. 14, 1993, now U.S. Pat. No. 5,447,868 issued Sep. 5, 1995.

This invention relates to the detection of fecal occult blood, and in particular to the use of enhanced developers in the detection of fecal occult blood.

Fecal occult blood may provide a reliable diagnostic indicator of a variety of medical conditions involving gastrointestinal bleeding which may otherwise be difficult to detect, including colorectal cancer. The use of this method is well described in the medical literature. See e.g., Greegor, D. H., Cancer 19:330–337 (1969) and Hastings, J. B., Amer. J. Surg. 127:228–233 (1974). Tests for fecal occult blood based upon the oxidation of guaiac to form a blue colored product in the presence of hydrogen peroxide and hemoglobin have been described in U.S. Pat. No. 3,996,006, incorporated herein by reference. Such products are sold under the trademarks HEMOCCULT® AND SERACULT®. Briefly, the test involves placing a fecal sample on an absorbent paper coated with guaiac and adding a developer solution containing hydrogen peroxide. If hemoglobin is present, the guaiac is oxidized, turning the paper blue.

It is considered desirable to increase the sensitivity of the test in order to detect excessive blood loss into the bowel at the earliest possible stage. The occurrence of false negatives, the problem of not detecting the presence of blood, is thus detrimental. Attempts have therefore been made to increase the sensitivity of the test. For example, the addition of a drop or two of water to the fecal smear on the guaiac impregnated test paper prior to the addition of the peroxide solution has been used to enhance the test sensitivity. Such procedures frequently give a positive reaction even if there is no pathologically significant amount of blood present in the stool. The occurrence of false positives is also undesirable, since it can lead to unnecessary follow-up medical procedures.

An improved version of this test is described in European Patent Publication No. 0 308 227. Phenols are added to the developer solution to achieve an enhancement of the amount of colored product produced, resulting in a more sensitive assay.

SUMMARY OF THE INVENTION

It has now been found that compounds other than phenols, specifically tertiary and quaternary nitrogen compounds, can be used to enhance the sensitivity of a test for fecal occult blood. It is therefore an object of the present invention to provide an enhanced method for testing of fecal occult blood that makes use of (1) monocyclic nitrogen-containing aromatic heterocyclic compounds such as triazole, pyridine, pyrazine or substituted derivatives thereof; (2) tertiary or quaternary ammonium compounds containing at least one hydroxy alkyl or esterified hydroxy alkyl group or a phenyl or substituted phenyl group to the nitrogen or (3) quinoline or a substituted derivative thereof to enhance the sensitivity of the test.

It is a further object of the invention to provide a developer solution containing an enhancer in accordance with the invention together with peroxide in an ethanol water carrier for use in testing for fecal occult blood.

It is still a further object of the invention to provide a kit for testing for fecal occult blood. Such a kit includes an enhanced developer composition containing an enhancer according to the invention and an oxidizable substrate such as guaiac.

DETAILED DESCRIPTION OF THE INVENTION

In accordance with the present invention, a fecal specimen may be tested for the presence of occult blood by combining the fecal specimen with (a) an oxidizable substrate that produces a colored product in the presence of peroxide and hemoglobin;

(b) hydrogen peroxide or a peroxide source; and (c) an enhancer selected from the group consisting of monocyclic nitrogen-containing aromatic heterocyclic compounds or tertiary or quaternary ammonium compounds which enhance the sensitivity of the test. If hemoglobin is present in the fecal sample, the oxidizable substrate is converted to the visibly detectable, colored product.

A preferred oxidizable substrate for use in accordance with the invention is guaiac which is the substrate used in commercially available test kits. Other substrates which are oxidized by peroxide in the presence of hemoglobin to produce a colored product that can be visually detected in the presence of fecal material may also be used. Suitable alternative materials include 3,3", 5,5-tetramethylbenzidine (see U.S. Pat. No. 4,562,043 incorporated herein by reference), guaiaconic acid A and other leuco dyes that are oxidized in the presence of peroxide and hemoglobin (see U.S. Pat. Nos. 4,219,336 and 4,971,914 incorporated herein by reference).

A simple and convenient way to conduct the test is to place the oxidizable substrate on a solid support. A preferred solid support is an absorptive paper which has been impregnated with the oxidizable substrate. The oxidizable substrate needs to be present in amounts sufficient to generate a detectable amount of colored product, generally above 0.5 gm/1000 in$^2$. In the coated paper used in commercial kits today, this amounts to about 0.75 gm/1000 in$^2$. Using a micropipet, a small (e.g. 0.03 ml) aliquot of the fecal specimen is placed on the support. One or two drops of developer solution are then added, and the extent of color development, if any, is observed.

This developer solution contains hydrogen peroxide or a source of peroxide such as cumene hydroperoxide and the enhancer in an ethanol/water carrier. The developer solutions of the invention generally contain 4 to 6% by weight of hydrogen peroxide, 0.2 to 4% by weight of the enhancer, and 80 to 90% ethanol with the balance being water. Preferably, the enhancer will be present in amounts of from 0.3 to 1.5% by weight, the exact amount depending on the specific enhancer being used. Unless limited by solubility considerations, higher enhancer concentrations can also be used but it will be appreciated that the resulting increase in sensitivity may lead to the detection of low levels of occult blood that are not medically significant, i.e., false positives.

Enhancers useful in the present invention include monocyclic nitrogen-containing aromatic heterocyclic compounds such as triazole, pyridine, pyrazine and substituted derivatives thereof, including 4-benzyl pyridine, 2-methoxy pyridine, 4-(p-nitrobenzyl) pyridine, and pyrazine carboxylic acid. Other enhancers in accordance with the invention are tertiary or quaternary amines having at least one hydroxy alkyl or esterified hydroxy alkyl group attached to the nitrogen. Examples of such enhancers include diethyl ethanolamine, ethyl diethanolamine and triethanolamine, acetylcholine chloride and β-methyl acetylcholine chloride. A further class of enhancers in accordance with the present invention are tertiary and quaternary amines having a phenyl group attached to the nitrogen, e.g. dimethyl aniline. Quinoline and derivatives thereof such as alpha-hydroxy quinoline were also found to be effective enhancers.

EXAMPLE 1

Various compounds were tested for their ability to act as enhancers of guaiac oxidation by peroxide in the presence of hemoglobin. A sample of blood was diluted 1:20,000 to approximate the level of blood in a fecal sample and an 0.03 ml drop was placed onto a guaiac coated paper support of the type used in SERACULT® and SERACULT PLUS® test kits. 1–2 drops of a developer solution (0.04 to 0.1 ml) containing 4% $H_2O_2$, 4% of a selected enhancer, 8% water and 84% ethanol was then placed on the paper support and observations for color formation were made. Each enhancer was rated on a scale of 1 to 4 for color formation, with 1 being the amount of color generated using no enhancer and 2 being the amount of color generated using 1.5% ethyl hydroxybenzoic acid (ethyl paraben), a phenolic enhancer of the type disclosed in EP 0 308 227 and used in commercial products. The results of these tests are shown in Table 1. In Table 1, an observable color intensity less than that of the unenhanced control is reported as TR.

During these tests, it was observed that the colored product produced varied in stability depending on the enhancer. The rate of fading is also reported in Table 1(VS=very slow, S=slow, M=moderate, F=fast). In general, a fade rate of moderate or slower is consistent with the ordinary period for observing the results of fecal occult blood tests of 30–120 seconds after testing.

TABLE 1

| Test Enhancer | Color Intensity | FADE |
| --- | --- | --- |
| 2 - methoxy pyridine | 3.5 | S |
| 3 - hydroxypyridine | 2.5 | S |
| 3 - hydroxypyridine-N-oxide | 1 | S |
| 4 - benzyl pyridine | 4 | S |
| pyridine | 3.5 | S |
| pyrazine | 4 | S |
| 1,2,4 - triazole | 3.5 | S |
| pyrazine carboxylic acid | 4 | S |
| quinoline | 3.5 | S |
| 2 - amino pyridine | tr | F |
| 4 - (p-nitrobenzyl)-pyridine (light yellow) | 3.5 | S |
| pyridine - HCl | 2.5 | F |
| dimethyl ethanolamine | 3.5 | S |
| triethanolamine | 1+ | M-S |
| phenyl diethanolamine | 3.5 | S |
| 8-hydroxy quinoline | 3 | S |
| Comparative Compounds | | |
| phenyl salicylate | 4 | S |
| salicylic acid | tr | S |
| hydroquinone | 0 | |
| methylether hydroquinone | tr | S |
| dimethyl hydroquinone | 1 | S |
| p-phenyl phenol | 2.5 | VS |
| 1,2 - dimethoxyphenol | tr | S |
| salicylamide | 1.5 | S |

EXAMPLE 2

An 0.03 ml drop of 1:30,000 diluted blood sample was placed on guaiac coated paper. One to two drops of a developer solution containing 84% ethanol, 4% hydrogen peroxide and 0.7% pyrazine carboxylic acid, the balance being water, was placed on the test paper. A blue coloration was observed where the blood sample had been placed on the test paper.

EXAMPLE 3

An 0.03 ml drop of a 1:30,000 dilution blood sample was placed on a guaiac-coated test paper. One to two drops of a developer solution containing 84% ethanol, 4% hydrogen peroxide, 0.5% 4-benzyl pyridine, the balance being water was then placed on the paper. A blue coloration was observed where the blood sample had been placed on the test paper.

EXAMPLE 4

Additional enhancers were tested using a 1:25,000 dilution of a blood sample. The results are summarized in Table 2.

TABLE 2

| Enhancer | Color Developed | Comments |
| --- | --- | --- |
| 1% acridine | 2 | developer is yellow but does not disturb result |
| 1% dimethylethanolamine | 2.5 | |
| 1.3% diethylethanolamine | 2.5 | |
| 4% diethylethanolamine | 1.5 | faded fast |
| 1% phenyldiethanolamine | 4 | |
| 1% dimethyl aniline | 2.5 | faded fast |
| 4% triethanolamine | 1 | |
| 4.3% acetyl choline chloride | 1.5 | |
| 4% beta-methyl acetyl choline chloride | 1.5 | |
| 4% acetyl choline bromide | .5 | |
| Controls | | |
| Seracult | <.5 | |
| Seracult + 1.5% ethyl paraben | 1 | |

EXAMPLE 5

Because peroxide may be lost from developer solutions on aging, developer solutions with lower levels of peroxide were tested. Three sets of developer solutions were prepared for each enhancer tested containing 2%, 3% and 4% hydrogen peroxide by mixing 44 grams ethanol, 0.04 g phosphoric acid, 0.3 to 2 grams of an enhancer and 0.32, 0.47. or 0.63 grams of peroxide and adding water to a total weight of 50. The results, summarized in Table 3, show that lower peroxide concentrations can be effectively used.

TABLE 3

| Enhancer | Peroxide Concentration | | | Persistence of Blue color |
| --- | --- | --- | --- | --- |
| | 4% | 3% | 2% | |
| ethyl paraben (1.5%) | 3+ | 3+ | 3+ | slow fade |
| benzophenone (4%) | 1+ | 1+ | 1+ | slow fade |
| dimethyl ethanolamine (1%) | 3+ | 3+ | 3+ | fast fade |
| benzyl pyridine (1%) | 4+ | 4+ | 4+ | medium fade |
| pyrazine (1%) | 4+ | 4+ | 4+ | medium fade |
| pyrazine carboxylic acid (0.6%) | 3.5+ | 3.5+ | 3.5+ | slow fade |

EXAMPLE 6

To evaluate the storage stability of developer solutions according to the invention, developers containing various enhancers was refluxed for 48 or 65 hours and tested for the level of peroxide. The average starting peroxide level was 4.27% The samples which had been refluxed for 65 hours were also tested for their usefulness in developing a fecal occult blood test. The results, which are summarized in Table 4, show the stability of various enhancers in accordance with the invention, although triazole had poor results in this rather extreme test.

TABLE 4

| Enhancer | $H_2O_2$ (%) after 48 hours | $H_2O_2$ (%) after 65 hours | COLOR SCORE W/O REFLUX | COLOR SCORE W/ REFLUX |
|---|---|---|---|---|
| 1.23% 4-benzyl pyridine | 3.48 3.16 | 3.25 3.5 | 4+ | 3+ |
| 1% 4(p-nitro-benzyl) pyridine | 4.57 4.65 | 4.14 nd | 4+ | 3+ |
| dimethyl-ethanolamine | nd 1.93 | 1.62 1.57 | 3+ | 3+ |
| 1.1% 1,2,4 triazole | <.082 | | 4+ | 0 |
| benzophenone | 1.74 1.8 | nd nd | 1+ | 1+ |

EXAMPLE 7

The test of Example 6 was repeated but with a 72 hour reflux period and different enhancers. The results are summarized in Table 5.

TABLE 5

| Enhancer | Initial Peroxide (%) | $H_2O_2$ (%) after 72 hours | COLOR SCORE W/O REFLUX | COLOR SCORE W/ REFLUX |
|---|---|---|---|---|
| 0.6% pyrazine carboxylic acid | 4.27 | 4.14 4.27 | 3+ | 2+ |
| no enhancer | 4.27 | 1.88 2.1 | 2+ | 1+ |
| Seracult ® Plus | 4.09 | 2.62 2.45 | 3+ | 2+ |
| SANSA ® (Lot 5017C) | 4.11 | 2.97 2.95 | 2–3+ | 2+ |

I claim:

1. A method for detecting occult blood in a specimen comprising combining the specimen with
   (a) an oxidizable substrate that produces a colored product in the presence of peroxide and hemoglobin; and
   (b) a liquid developer comprising hydrogen peroxide or a peroxide source, a carrier consisting essentially of water and ethanol, and an enhancer component, said enhancer component consisting of a material selected from the group consisting of tertiary and quaternary amines having a hydroxy alkyl or esterified hydroxy alkyl group attached to the nitrogen, wherein the oxidizable substrate and liquid developer are combined with the specimen in amounts effective to produce a visually detectable color change if medically significant amounts of blood are present in the specimen.

2. A method according to claim 1, wherein the enhancer component is present in the carrier in amounts of from 0.2% to 4% by weight.

3. A method according to claim 1, wherein the enhancer component is present in the carrier in amounts of from 0.3% to 1.5% by weight.

4. A method according to claim 1, wherein the enhancer component is phenyl diethanolamine.

5. A method according to claim 1 wherein the enhancer component is dimethyl ethanolamine.

6. A composition for use as a developer in a test for occult blood based upon the oxidation of a substrate to a colored product comprising
   (a) hydrogen peroxide or a peroxide source;
   (b) an amount of an enhancer component effective to enhance the amount of colored product produced; and
   (c) a carrier consisting essentially of water and ethanol, wherein the enhancer component consists of a material selected from the group consisting of tertiary and quaternary amines having a hydroxy alkyl or esterified hydroxy alkyl group attached to the nitrogen.

7. A composition according to claim 6, wherein the enhancer component is present in amounts of from 0.2% to 4% by weight.

8. A composition according to claim 7, wherein the peroxide is present in an amount of from 4% to 6% by weight.

9. A composition according to claim 6, wherein the peroxide is present in an amount of from 4% to 6% by weight.

10. A composition according to claim 6, wherein the enhancer component is phenyl diethanolamine.

11. A composition according to claim 6, wherein the enhancer component is dimethyl ethanolamine.

12. A kit for the detection of occult blood comprising, in packaged combination,
    (a) an oxidizable substrate which is converted to a colored product in the presence of peroxide and hemoglobin; and
    (b) a liquid developer comprising hydrogen peroxide or a peroxide source and an enhancer component in an amount effective to enhance the conversion of the oxidizable substrate to the colored product in a carrier consisting essentially of ethanol and water, wherein the enhancer component consists of a material selected from the group consisting of tertiary and quaternary amines having a hydroxy alkyl or esterified hydroxy alkyl group attached to the nitrogen.

13. A kit according to claim 12, wherein the enhancer component is present in the developer in an amount of from 0.2% to 4% by weight.

14. A kit according to claim 13, wherein the peroxide is present in the developer in an amount of from 4% to 6% by weight.

15. A kit according to claim 12, wherein the peroxide is present in the developer in an amount of from 4% to 6% by weight.

16. A kit according to claim 12, wherein the enhancer component is phenyl diethanolamine.

17. A kit according to claim 12, wherein the enhancer component is dimethyl ethanolamine.

* * * * *